US010426485B2

United States Patent
Lorenzo

(10) Patent No.: US 10,426,485 B2
(45) Date of Patent: Oct. 1, 2019

(54) EMBOLIC COIL DETACHMENT MECHANISM WITH HEATING ELEMENT AND KICKER

(71) Applicant: DEPUY SYNTHES PRODUCTS, INC., Raynham, MA (US)

(72) Inventor: Juan Lorenzo, Davie, FL (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 404 days.

(21) Appl. No.: 14/847,296

(22) Filed: Sep. 8, 2015

(65) Prior Publication Data

US 2015/0374382 A1 Dec. 31, 2015

Related U.S. Application Data

(62) Division of application No. 13/436,289, filed on Mar. 30, 2012, now Pat. No. 9,155,540.

(51) Int. Cl.
*A61B 17/12* (2006.01)
*A61B 17/00* (2006.01)

(52) U.S. Cl.
CPC .... *A61B 17/12113* (2013.01); *A61B 17/1214* (2013.01); *A61B 17/12022* (2013.01); *A61B 2017/00951* (2013.01); *A61B 2017/1205* (2013.01); *A61B 2017/12054* (2013.01); *A61B 2017/12068* (2013.01)

(58) Field of Classification Search
CPC .. A61B 2017/1209; A61B 2017/12077; A61B 2017/12072; A61B 2017/12068; A61B 2017/12063; A61B 2017/12059; A61B 2017/12054; A61B 2017/1205
See application file for complete search history.

(56) References Cited

U.S. PATENT DOCUMENTS

| 5,108,407 A | 4/1992 | Geremia |
| 5,578,074 A | 11/1996 | Mirigian |
| 5,911,737 A | 6/1999 | Lee |
| 5,944,733 A | 8/1999 | Engelson |
| 5,989,242 A | 11/1999 | Saadat |
| 6,059,815 A | 5/2000 | Lee |
| 6,102,933 A | 8/2000 | Lee |

(Continued)

FOREIGN PATENT DOCUMENTS

| CN | 1874739 A | 12/2006 |
| JP | 2002017736 A | 1/2002 |

(Continued)

*Primary Examiner* — Christopher L Templeton

(57) ABSTRACT

Provided herein are a system, method, and apparatus for delivering a therapeutic device, e.g. an embolic coil, from a delivery tube at a target site in a patient's body. A heating element is disposed in the delivery tube that can be actuated remotely, and a layer of low temperature adhesive is applied at the heating element to retain the therapeutic device. The kicker in the form of, for example, a compressed spring is mounted within the delivery tube so as to be in contact with the therapeutic device for applying a constant ejector force that is countered by the adhesive force of the low temperature adhesive. When the heating element is actuated, the spring's ejector force overcomes the softened adhesive's adhesive force to force the therapeutic device out of the delivery tube.

7 Claims, 2 Drawing Sheets

(56) References Cited

U.S. PATENT DOCUMENTS

| | | |
|---|---|---|
| 6,149,664 A | 11/2000 | Kurz |
| 6,575,965 B1 | 6/2003 | Fitch |
| 6,743,236 B2 | 6/2004 | Barry |
| 6,743,251 B1 | 6/2004 | Eder |
| 7,344,558 B2 | 3/2008 | Lorenzo |
| 7,578,826 B2 | 8/2009 | Gandhi |
| 7,582,101 B2 | 9/2009 | Jones |
| 7,591,833 B2 | 9/2009 | Jones |
| 7,744,604 B2 | 6/2010 | Maitland |
| 7,776,054 B2 | 8/2010 | Gandhi |
| 7,780,680 B2 | 8/2010 | Gandhi |
| 7,819,891 B2 | 10/2010 | Balgobin |
| 7,819,892 B2 | 10/2010 | Balgobin |
| 7,972,342 B2 | 7/2011 | Gandhi |
| 7,985,238 B2 | 7/2011 | Balgobin |
| 2002/0133189 A1* | 9/2002 | Gifford, III ...... A61B 17/12022 606/191 |
| 2004/0034363 A1 | 2/2004 | Wilson |
| 2005/0149108 A1 | 7/2005 | Cox |
| 2006/0025801 A1 | 2/2006 | Lulo |
| 2006/0052815 A1* | 3/2006 | Fitz .................... A61B 17/0057 606/200 |
| 2006/0200192 A1 | 9/2006 | Fitz |
| 2007/0106323 A1 | 5/2007 | Barry |
| 2007/0239196 A1 | 10/2007 | Pomeranz |
| 2007/0299422 A1* | 12/2007 | Inganas ............. A61B 17/0057 604/508 |
| 2008/0300616 A1 | 12/2008 | Que |
| 2009/0270903 A1 | 10/2009 | Litzenberg |
| 2010/0160944 A1 | 6/2010 | Teoh |
| 2010/0268204 A1* | 10/2010 | Tieu ................. A61B 17/12022 606/27 |
| 2011/0060360 A1 | 3/2011 | Mitelberg |

FOREIGN PATENT DOCUMENTS

| | | |
|---|---|---|
| JP | 2006181088 A | 7/2006 |
| WO | WO 2005108635 A2 | 11/2005 |
| WO | WO 2011130081 A1 | 10/2011 |

* cited by examiner

EMBOLIC COIL DETACHMENT MECHANISM WITH HEATING ELEMENT AND KICKER

CROSS REFERENCE TO RELATED APPLICATION

The present application is a divisional of U.S. application Ser. No. 13/436,289 filed Mar. 30, 2012.

BACKGROUND

The present invention relates to a medical device for placing an embolic coil at a preselected location within a vessel of the human body, and more particularly, relates to a flexible delivery member having a heating element and an ejecting member at the distal end of the delivery member for delivering the embolic coil at the preselected location.

Elongate flexible catheters are used to place various devices within the vessels of the human body. Such devices include dilatation balloons, radiopaque fluids, liquid medications and various types of occlusion devices such as balloons and embolic coils. Occlusion devices including embolic coils can be used to treat aneurysms or to occlude the blood vessel at a target location.

Coils which are placed in vessels may take the form of helically wound coils, or alternatively, may be randomly wound coils, convoluted coils, coils wound within other coils or many other such configurations to better occlude a blood vessel. Embolic coils are generally formed of radiopaque biocompatible metallic materials, such as platinum, gold, tungsten, or alloys of these metals. The coils can be coated with various materials to improve their thrombogenicity. Often times, several coils are placed at a given location in order to occlude the flow of blood through the vessel by promoting thrombus formation at the particular location. The decreased blood flow reduces the pressure on the aneurysm and reduces the risk of a ruptured aneurysm.

In the past, embolic coils have been placed within the distal end of the catheter. When the distal end of the catheter is properly positioned the coil may then be pushed out of the end of the catheter with, for example, a guidewire, to release the coil at the desired location. This procedure of placement of the embolic coil is conducted under fluoroscopic visualization such that the movement of the coil through the vasculature of the body may be monitored and the coil may be placed at the desired location. With these placements systems there is very little control over the exact placement of the coil since the coil may be ejected to a position some distance beyond the end of the catheter. Further, ejecting the embolic coil with a guidewire can be problematic as the coil and guidewire shift during movement along the patient's vascular system.

Patients with potentially life-threatening hemorrhagic brain aneurysms are in need of a safe, reliable, and accurate release mechanism for the deposition of embolic coils via catheters. Numerous procedures have been developed to enable more accurate positioning of coils within a vessel. One commercial product of current use is the Guglielmi Detachable Coil (GDC). The GDC utilizes the electrolytical dissolution of a designated guidewire junction to generate the release action. This procedure typically takes 10-30 minutes and is difficult to control in a reliable fashion. The effects of the dissolved material in the blood stream create a potential hazard to the patient. Problems that have been associated with the release of the coil include the force of the coil exiting the delivery catheter causing the coil to overshoot the desired site or dislodge previously deployed coils. Thus, even with the numerous prior efforts to develop miniature actuators for catheter-based therapeutic application, there remains a need for a safe, accurate release actuator mechanism for the delivery of embolic coils.

Another problem with embolic coil delivery systems that rely on a stiff pusher wire extending through the entire length of the catheter to push an element out of the distal end of the catheter is that the pusher wire inherently causes the catheter to be very stiff, with the result that it is very difficult to guide the catheter through the vasculature of the body. Accordingly, there is a need for a mechanism for deploying embolic coils from the distal end of a catheter having a flexible body that does not inhibit the navigation of the catheter distal end through the tortuous path of a patient's vasculature.

There is also a need for precise therapeutic actuators configured to deploy therapeutic elements or devices, e.g. embolic coils, within the narrow confines of blood vessels in the human brain, e.g. 250-500 micrometers in diameter. The present invention satisfies these and other needs.

SUMMARY OF THE INVENTION

Briefly and in general terms, the present invention provides for a release mechanism, a therapeutic actuator, or a system for delivering a therapeutic element or device to a target location. The target location is a site within the vasculature of the human body, for example, a blood vessel in the brain in order to treat an aneurysm.

In its most basic form, the release mechanism includes a therapeutic element, such as an embolic coil, having an embolic component mounted on an extension fitting that includes a peg depending from the proximal end of the embolic coil. The peg of the extension fitting is retained in the distal end of a catheter body by a low temperature adhesive, which affixes the extension fitting to a cylindrical heating element. The peg of the extension fitting is also in contact with a compressed spring so as to apply a distally directed force against the extension fitting and the embolic coil mounted thereon. The force of the spring is sufficient to eject the extension fitting from the catheter body, but insufficient to overcome the adhesion of the extension fitting to the heating element via the low temperature adhesive. The heating element includes two electrical leads that extend to a proximal end of the catheter body, such that the heating element can be actuated from outside of the patient when the catheter body is deployed in the patient's vascular system.

When the distal end of the catheter body is positioned at the desired location for the embolic coil to be released, the heating element is actuated via the electrical leads causing heat to build up on the interface between the peg of the embolic coil's extension fitting and the heating element. This build-up of heat softens the low temperature adhesive until the bond between the heating element and the extension fitting weakens. As further heat is applied, the force on the peg of the extension fitting by the spring overcomes the adhesion to the heating element and the spring ejects the extension fitting and its mounted coil from the distal end of the catheter body at the desired location.

DETAILED DESCRIPTION OF THE PREFERRED EMBODIMENTS

Figure 1:
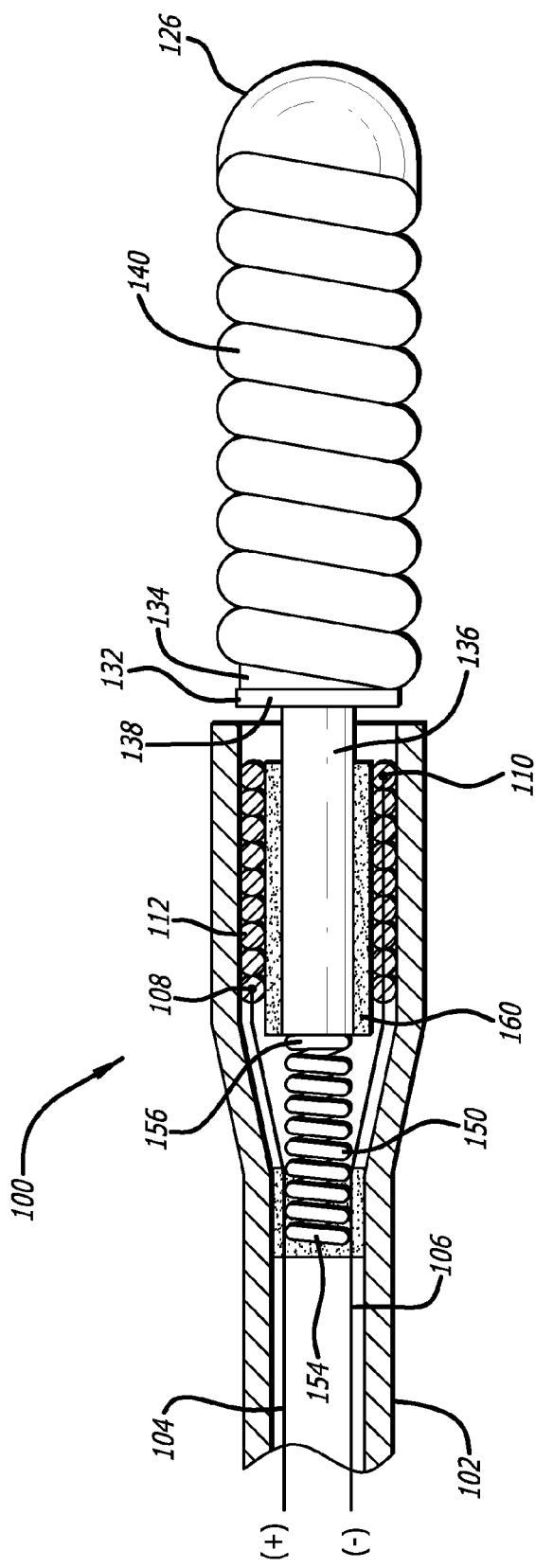
FIG. 1 is a side view of a system for delivery of a therapeutic device in accordance with an embodiment of the present invention with the therapeutic device mounted on an extension member affixed to a catheter body.
Figure 2:
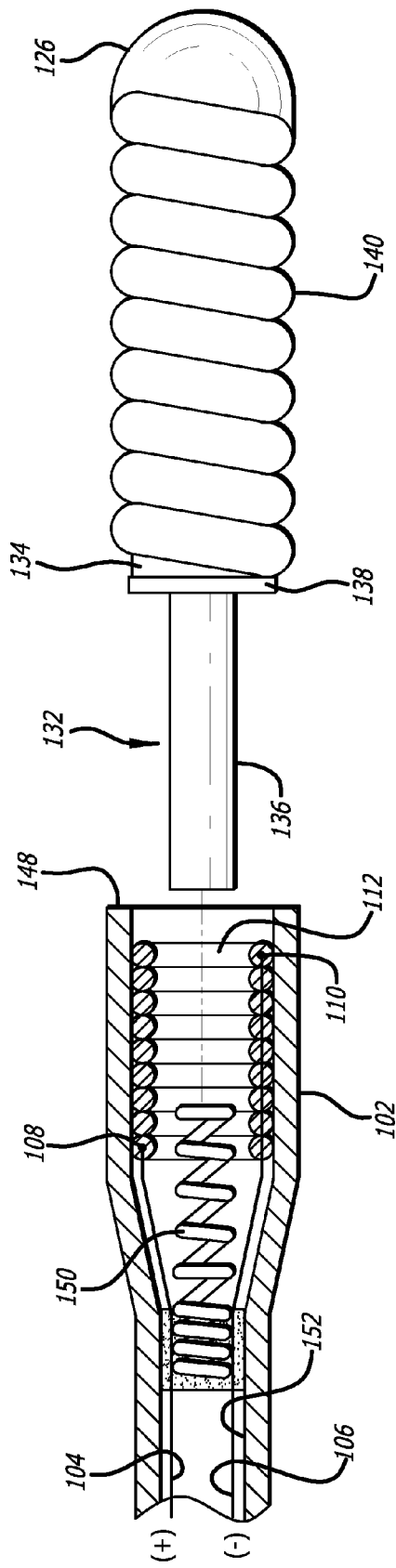
FIG. 2 is a side view of a system for delivery of a therapeutic device in accordance with an embodiment of the present invention with extension member released from the catheter body.

Referring to the drawings, which are provided by way of example, and not by way of limitation, the present invention provides for a therapeutic element delivery system 100 (which may also be referred to as a therapeutic actuator or a release mechanism) including a flexible tube 102 for delivering a therapeutic element 140 to a target site within a body and a release system that can be thermally decoupled to detach the therapeutic element 140 from the flexible tube 102. The therapeutic element 140 may be an embolic coil or another occlusive device that serves to occlude an aneurysm by filling the aneurysm pouch, creating a physical barrier to reduce blood flow into the aneurysm, and inducing thrombosis or clotting therein. The flexible tube 102, which may be a catheter body, may be flexible along its entire length or the flexible region may be restricted to the distal end of the tube.

The therapeutic element 140 can be formed with, or mounted on, an extension member 132 that includes a mounting portion 134 at the distal end that supports the therapeutic element 140, and a peg 136 that is received in the tube 102. The extension member serves to secure the therapeutic element 140 at the distal end of the flexible tube until it is ready to be deployed in the patient, as set forth more fully below.

The present invention allows the extension member 132 to be thermally decoupled from the flexible tube 102 to deploy the therapeutic element at a more precise location of the therapeutic element 140. Whereas prior art devices have relied upon pusher wires and other ejection mechanisms that exert an often uncontrollable and unpredictable force on the therapeutic element to deploy it, the thermally activated decoupling system can be quickly and easily decoupled without propelling the therapeutic element out of the delivery tube. This is desirable as uncontrolled therapeutic elements that prematurely release from the tube may result in inaccurately placed coils or coils that dislodge other previously placed coils.

Within the flexible tube 102, a pair of electrical conductors extend from a proximal end (not shown) to the distal end. For example, there may be a positively charged electrical conductor 104 and a negatively charged electrical conductor 106. The electrical conductors are attached to a thermally responsive heating element 112 such as a heating coil or the like through electrical contacts 108, 110. When an electrical current is directed through the conductors 104, 106, the thermally responsive element 112 begins to heat up. The conductors 104, 106 extend through the flexible tube 102 such that they can be actuated from outside the patient once the therapeutic device 140 is positioned in the desired location.

The extension member 132 is formed with, or have mounted thereon, a bead 126 at its distal end and a collar 138 at an intermediate portion, where the therapeutic device 140 is captured between the bead 126 and the collar 138. A distal outer surface of the bead 126 may be substantially hemispherical, curved, or rounded so as to facilitate an atraumatic introduction of the therapeutic element 140. The bead 126 holds the therapeutic element 140 in a compressed configuration by compressing the therapeutic element 140 against the distal end 148 of the flexible tube 102, or between the bead 126 and the collar 138. In the case where the therapeutic element 140 is compressed between the bead 126 and the distal end 148 of the flexible tube, when the connection between the extension fitting 132 and the flexible tube 102 is severed via heating of the heating element 112, the therapeutic element 140 can expand and occupy its intended position in the patient's vasculature. In an alternate embodiment, at least a portion of the therapeutic element 140 also is located within the distal end 148 of the flexible tube 102.

The extension fitting 132, when disposed in the distal end 148 of the flexible tube 102, has a peg 136 that is adjacent a compressed spring 150. The proximal end 154 of the spring 150 is fixed to the inner surface 152 of the flexible tubular member 102 by an attachment means such as adhesive, whereas the distal end 156 of the spring 150 is free to extend distally away from the fixed proximal end. As shown in FIG. 1, the peg 136 of the extension fitting 132 bears against the distal end 156 of the spring 150 when the extension fitting 132 is in the delivery position, such that the spring 150 applies a force on the extension fitting 132 at the proximal end of the peg 136 tending to push the extension fitting 132 out of the flexible tube 102. The extension fitting 132 is retained in the flexible tube 102 by virtue of the low temperature adhesive 160 that bonds the peg 136 of the extension fitting 132 to the thermally responsive heating element 112. The force of the spring 150 on the peg 136 is insufficient to overcome the bonding strength of the low temperature adhesive 160 under nominal conditions. Thus, the therapeutic element 140 can be safely and securely delivered to the placement site as it is carried on the extension fitting 132 until it is ready to be released to the treatment site.

Once the flexible tube reaches the treatment site and the therapeutic element is to be released, the conductors 104, 106 are actuated from the proximal end of the flexible tube 102. As current passes through the conductors 104, 106, the thermally responsive heating element 112 begins to heat up, and in heating up it softens the low temperature adhesive 160. Epoxies are examples of such low temperature adhesives, and in a preferred embodiment the adhesive 160 has a softening temperature of no less than sixty degrees Celsius. As the low temperature adhesive 160 softens, the force of the spring 150 overcomes the bonding force of the adhesive 160, and the spring 150 ejects the extension fitting 132 and the mounted therapeutic element 140 from the distal end 148 of the flexible tube 102. The therapeutic element 140 can then expand and, for example, fill the site of the embolism, thereby treating the condition. The flexible tube 102 can then be withdrawn from the patient, leaving the therapeutic element 140 in place along with the extension fitting 132. The extension fitting 132 will preferably be made of a biocompatible, absorbable material that will be absorbed by the body without causing any disruption of the blood flow.

According to one of several embodiments, the therapeutic element delivery system as described herein is capable of operating in small (250-500 micrometers) diameter applications, such as in veins in the human brain, which enables catheter-based devices to reach and treat an aneurysm in the brain.

It will be apparent from the foregoing that while particular forms of the invention have been illustrated and described, various modifications can be made without departing from the spirit and scope of the invention. For example, other types of ejection devices can be used besides a coil spring to eject the extension fitting from the flexible tube. Similarly, the therapeutic devices can be any number of devices that are intended to be deposited in a patient's vasculature. Accordingly, it is not intended that the invention be limited, except as by the appended claims.

I claim:

1. A catheter for delivering an embolic component, comprising:
   a flexible tubing defining a lumen, the flexible tubing having a proximal end and a distal end;
   a cylindrical heating element disposed at the distal end of the flexible tubing, said cylindrical heating element defining a channel therethrough, the cylindrical heating element including electrical conductors extending along the flexible tubing in a longitudinal direction; and
   a spring disposed in the flexible tubing and proximal to the cylindrical heating element in a compressed condition, the spring having a proximal end and a distal end, the proximal end of the spring being fixed within the flexible tubing and the distal end of the spring being configured for longitudinal movement within the flexible tubing, the distal end of the spring extending within a portion of the channel defined by the cylindrical heating element in an uncompressed condition.

2. The catheter of claim 1 wherein the cylindrical heating element includes a layer of low temperature adhesive on an inner surface.

3. The catheter of claim 2 wherein the low temperature adhesive has a softening temperature no less than sixty degrees Celsius.

4. The catheter of claim 1 further comprising an embolic coil device at least partially disposed within the distal end of the flexible tubing.

5. The catheter of claim 4 wherein the embolic coil device includes a working portion and a securing portion, the securing portion is sized to be retained within the channel of the cylindrical heating element.

6. The catheter of claim 5 wherein the securing portion is held within the flexible tubing by a layer of low temperature adhesive.

7. The catheter of claim 5 wherein the working portion of the embolic coil device is external to the flexible tubing.

* * * * *